United States Patent

Rusakova et al.

[11] Patent Number: 4,518,592
[45] Date of Patent: May 21, 1985

[54] PROCESS FOR PREPARING MANGIFERIN

[76] Inventors: Svetlana V. Rusakova, 3, kv. 49, poselok Polyany, Moskovskaya oblast; Vladimir I. Glyzin, ulitsa Shipilovskaya, 29, korpus 2, kv. 255, Moscow; Stepan I. Kocherga, ulitsa Botanicheskaya, 8, kv. 7, p/o Vilar, Moskovskaya oblast; Alla A. Ananieva, Birjulevskaya ulitsa, 5, korpus 2, kv. 463, Moscow; Larisa F. Libizova, ulitsa Botanicheskaya, 8, kv. 8, p/o Vilar, Moskovskaya oblast, all of U.S.S.R.

[21] Appl. No.: 494,138

[22] Filed: May 16, 1983

Related U.S. Application Data

[63] Continuation of Ser. No. 283,396, Jul. 15, 1981, abandoned.

[30] Foreign Application Priority Data

Jul. 16, 1980 [SU] U.S.S.R. .............................. 2960018

[51] Int. Cl.$^3$ ............................................. A61K 35/78
[52] U.S. Cl. ................................................. 424/195.1
[58] Field of Search ........................................ 424/195

[56] References Cited

U.S. PATENT DOCUMENTS 3,772,269 11/1973 Lew ......................................... 536/4

FOREIGN PATENT DOCUMENTS 0197712 12/1977 U.S.S.R. ................................. 536/8

OTHER PUBLICATIONS

Komarov, Flora of the USSR, 1948, Izdatelstvo Akademii Naak SSSR Pub., pp. 278–279.
British Pharmacopoeia, 1980, vol. 2, pp. 561–565.

Primary Examiner—Albert T. Meyers
Assistant Examiner—John W. Rollins, Jr.
Attorney, Agent, or Firm—Ladas & Parry

[57] ABSTRACT

A process for preparing mangiferin from plants of the genus of Hedysarum (*Hedysarum alpinum L., Hedysarum flavescens Rgl. et Schmalh*) comprising extraction of xanthone glycosides from the aerial portion of the plants by means of a mixture acetone-water at a volume ratio of the mixture components of 1:0.5–2 respectively; the resulting extract is evaporated, the evaporated extract is filtered. To the filtered evaporated extract sulphuric acid is added to a pH of from 2 to 4, heated at reflux and filtered. The thus-prepared extract is treated with a non-polar organic solvent with the formation of two layers, wherefrom the upper aqueous layer contains xanthone glycosides. This upper layer is treated with butanol with the formation of two layers, wherefrom the upper layer comprises a solution of xanthone glycosides in butanol. This upper butanolic layer is evaporated. The precipitated mangiferin is separated and recrystallized.

1 Claim, No Drawings

PROCESS FOR PREPARING MANGIFERIN

This is a continuation of co-pending application Ser. No. 283,396 filed July 15, 1981, now abandoned.

FIELD OF THE INVENTION

The present invention relates to processes for preparing mangiferin.

Mangiferin (xanthone glycoside) can be useful in medicine as a medicated compound for the treatment of viral diseases of skin and mucous membranes.

BACKGROUND OF THE INVENTION

Known in the art a number of processes for the preparation of mangiferin. One of the processes consists in that from the disintegrated serial part of a plant belonging to the genus of *Hedysarum alpinum L.* xanthone glycosides are extracted with 80% ethanol. The extraction is effected upon heating at reflux on a water bath. The starting material and the extraction agent are taken in the amount of 1 kg of the starting plant material per 10 liters of the extraction agent. The resulting extract is partly evaporated. The evaporated extract is treated with water and then purified by chloroform. As a result two layers are formed, wherefrom the upper one contains xanthone glycosides. The layers are separated. From the upper layer mangiferin is isolated chromatographically on a polyamide. To this end, the upper layer is placed into a column and eluted with an ethanol-water mixture. The ethanolic eluates containing mangiferin are evaporated and recrystallized from a mixture dioxane-water (volume ratio of 1:1). The yield of mangiferin produced by this process is 0.5% by weight of the starting material (see V. B. Kuvaev, V. I. Glysin, G. S. Glysina, A. I. Ban'kovsky "Vegetable Resources", 1972, vol. 8).

This process results in the production of mangiferin of a sufficiently high purity grade. However, the use of sorption techniques for separation and purification of xanthone glycosides in the above process hinders the preparation of mangiferin and makes it economically inefficient.

Also known in the art is another process for the production of mangiferin. In this process from the disintegrated aerial portion of a plant of the species *Hedysarum alpinum L.* or *Hedysarum flavescens Rgl. et Schmalh.* xanthone glycosides are extracted by means of aqueous 80% ethanol for several times (up to four) at the temperature of 70° C. The combined extracts are evaporated. After the filtration the evaporated extract is placed into a division funnel and treated with a non-polar solvent such as chloroform. This operation is carried out for the purification of the extract from chlorophyll and other non-polar compounds contained in the vegetable stock. As a result, two layers are formed. The layers are separated. The upper aqueous layer contains xanthone glycosides. Then the upper layer is placed into a funnel, added with butanol, the mixture is stirred and allowed to stratify. The butanolic layer (upper) comprising a solution of xanthone glycosides in butanol is separated. This extraction of xanthone glycosides is carried out for several times. The combined butanolic solutions are evaporated to a predetermined volume so that mangiferin precipitates. The resulting mangiferin is recrystallized from a mixture of solvents—dioxane-water at the volume ratio thereof of 1:1. The yield of mangiferin in this process is 0.66% by weight of the starting vegetable stock (cf. S. V. Rusakova, V. I. Glysin, S. I. Kocherga, O. V. Soldatova, V. M. Mulevich, USSR Inventor's Certificate No. 596242 of Nov. 15, 1977).

One of the advantages of this process resides in replacement of a complicated and expensive chromatographic equipment for isolation of mangiferin by a liquid-phase extraction with an organic solvent. This has made it possible to increase the yield of mangiferin. However, its yield is still insufficient. This is due to the fact that during extraction of xanthone glycosides with butanol accompanying compounds, i.e. flavonol-O-glycosides also pass into the extract along with mangiferin. The presence of these compounds in the extract hinders separation of mangiferin from the evaporated butanolic solution. Furthermore, the process necessitates a repeated extraction of the vegetable stock with 80% ethanol.

Known is a process for extraction of xanthone glycosides from plants of the genus of Hedysarum by means of a mixture of acetone and water. In this case the process of extraction proceeds rather rapidly without application of an elevated temperature (cf. Proceedings of the All-Union Conference on Extraction, "Zinjate" Publishing House, Riga, 1977).

The plants *Hedysarum alpinum L.* and *Hedysarum flavescens Rgl. et Schmalh.* are described in the official publication "Flora of the USSR" compiled by E. G. Bobrov et al and published by Izdatelstvo Akademi Nauk SSSR Publishers, Moscow/Leningrad (1948). On page 278 of this publication *Hedysarum flavescens Rgl. et Schmalh.*, identified in 1881, is described as a yellowish plant of height up to 1.5 m. The plant is almost bare and except for several enlargements, the stalks are straight or slightly ascendenent and cylindrical. The stipules are scaly, joined with one another in lower leaves and free in upper leaves. The leaves have very short stalks and are arranged in 3 to 5 pairs, elongated egg-shaped or elliptical 20-35 (45) mm long, 17-20 (35) mm wide, rounded or obtuse at the vertex, with pointed ends. Floriferous shoots (together with raceme) are much longer than the leaves. The racemes are not thick, they have 15-35 flowers all being one-sided. The bracts are longer than the flowers before the blooming so that all racemes (in buds) look like a pappus. The bract cup is shorter than the peduncle at the end. The peduncles are thin, 3 to 5 mm long. The flowers are 15-20 mm long. The cup is bell shaped and the teeth of the cup are unequal: the lower teeth are longer than the cup tube and the upper ones are shorter. The corolla is yellow. The carpel of the flag is elongated or elongated and elliptical, slightly recessed at the vertex. The cover slip is longer than the flag and wings. The ovary is downy, on a long stem, with a few seed buds. The beans are on a stem with 2 to 4 flat segments which are elongated and elliptical or elongated, thin and reticular, having a wide integral wing at the edge and narrowing to the base. The pods are bud-like and flattened.

The plant is found in mixed-grass cereal plains, subalpine meadows, along banks of mountain rivers and at glaciers; predominantly in the subalpine zone at an altitude of 2500 to 3200 m.—location Mid. Asia. The type is in Legingrad.

The plant is valuable as an animal feed.

SUMMARY OF THE INVENTION

It is an object of the present invention to provide such a process for the preparation of mangiferin which would make it possible to obtain the desired product in a higher yield.

This and other objects of the present invention are accomplished by that in the process for the preparation of mangiferin from plants of the genus of Hedysarum (*Hedysarum alpinum L., Hedysarum flavescens Rgl. et Schmalh*) involving extraction of xanthone glycosides from the aerial part of plants by means of a mixture acetone-water at a volume ratio between the mixture components of 1:0.5–2 respectively, evaporation of the resulting extract, filtration of the evaporated extract, treatment of the extract with a non-polar organic solvent with the formation of two layers, wherefrom the upper aqueous layer contains xanthone glycosides, subsequent treatment of this upper layer with butanol to form two layers, wherefrom the upper layer comprises a solution of xanthone glycosides in butanol, evaporation of said upper butanolic layer, followed by separation of the precipitated mangiferin and recrystallization thereof, according to the present invention, prior to the treatment of the extract with the non-polar organic solvent it is added with sulphuric acid to a pH value of from 2 to 4 and heated at reflux, followed by filtration.

As used herein the expression "aeral part of the plants" is intended to mean that portion of the plant above the ground and will be referred to hereinafter by the more conventional term "foliage" which is generally defined to include leaves or leafage, flowers and stalks.

As it has been already mentioned hereinabove, prior to the treatment of the extract with a non-polar solvent it is added with sulphuric acid to pH of 2–4 and heated at reflux. Under these conditions there occurs hydrolysis of O-glycosides accompanying mangiferin. The aglycones formed as a result of hydrolysis are separated by filtration. These process steps make it possible to substantially increase the yield of the desired product.

The process for preparing mangiferin according to the present invention enables the production of the desired product in a yield of about 1% by weight of the estarting vegetable feedstock (by 34–50% higher than in the prior art processes).

DETAILED DESCRIPTION OF THE INVENTION

The process for preparing mangiferin according to the present invention is technologically simple and can be effected in the following manner.

Threshed disintegrated grass of the genus of Hedysarum such as *Hedysarum alphinum L.* or *Hedysarum flavescens Rgl. et Schmalh* with a particle size of from 2 to 5 mm is treated with a mixture acetone-water (volume ratio of 1:0.5–2 respectively) under continuous stirring and room temperature. The ratio between the vegetable feedstock and the solvent is selected within the range of from 1:10 to 1:20. The resulting aqueo-acetone extract is evaporated to $\frac{1}{4}$–1/6 of its initial volume, filtered to separate it from the residue of chlorophyll and resins. The filtered-off evaporated extract is acidified with sulphuric acid to a pH of from 2 to 4 under stirring, heated at reflux for 0.5 to 2 hours, cooled to room temperature for 1 to 3 hours to fully precipitate. Thereafter the extract is filtered. To the filtered-off extract a non-polar solvent such as dichloroethane or chloroform is added in several portions. As a result, two layers are formed and in the upper aqueous layer xanthone glycosides are contained. The layers are separated, the upper one is added with butanol saturated with water. This also results in the formation of two layers. The upper layer comprises a solution of xanthone glycosides in butanol. The layers are separated 3 to 7 such extractions are carried out altogether. The combined butanolic solutions are evaporated to 1/20–1/60 of their initial volume. A residue of mangiferin is formed which is cooled for a period of from 12 to 24 hours at a temperature within the range of from 3° to 12° C., filtered-off and recrystallized from a mixture of dioxane-water (1:0.5–1.2).

EXAMPLE 1

10 kf of threshed finely divided grass of *Hedysarum alpinum L.* with a particle size of not more than 3 mm are treated under continuous stirring for 15 minutes at room temperature with a mixture of acetone-water (1:1) at the ratio between the vegetable stock and the solvent of 1:17. 140 liters of aqueo-acetone extract are thus obtained. The vegetable feedstock is again extracted under the same conditions using the same mixture taken in the amount of 140 liters. The second aqueo-acetone extract is used for extraction of a fresh portion of the vegetable feedstock. The first water-acetone extract is evaporated in vacuum to bottoms having volume equal to 1/5 of the initial volume of the extract. The evaporated feedstock is filtered-off to separate it from the precipitated chlorophyll, resins and the like. The filtered extract is acidified with sulphuric acid to the pH of 2.9 and refluxed for one hour and then cooled to room temperature under stirring for 2 hours. Afterwards the extract is filtered to remove the precipitated residue. To the filtered-off extract there is added chloroform portion-wise for 3 times in portions of 10 l, 5 l and 5 l, 30 minutes for each portion. As a result, two layers are formed. In the upper aqueous layer xanthone glycosides are present. The layers are separated and the upper layer is added with butanol saturated with water in several steps: for the first extraction use is made of 10 liters, for the second and all other extractions—15 liters per each. There are carried out 5 extractions altogether lasting 30 minutes each. The combined butanolic solutions are evaporated in vacuum to the bottoms having volume equal to 1/40 of the initial volume. During evaporation a residue of mangiferin is formed. Mangiferin is filtered-off, disintegrated and recrystallized from a mixture dioxane-water (1:1). There is obtained 0.1 kg of mangiferin. The yield of mangiferin is equal to 1% by weight of the starting stock.

EXAMPLE 2

10 kg of threshed finely divided grass of *Hedysarum alpinum L.* with a particle size of not more than 5 mm are treated under continuous stirring with a mixture acetone-water (1:2) for 30 minutes at room temperature at the ratio between the starting feedstock and the solvent of 1:20. There are obtained 170 liters of a water-acetone extract. The starting feedstock is repeatedly extracted under the same conditions with 170 liters of the same mixture. The second water-acetone extract is used for extraction of a fresh portion of the feedstock. The first water-acetone extract is evaporated in vacuum to the bottoms having volume of 1/6 of the initial extract volume. The evaporated extract is filtered-off to separate it from precipitated chlorophyll, resins and the like. The filtered extract is acidified with sulphuric acid to the pH=2 and refluxed for 0.5 hour and then cooled to room temperature under stirring for 1 hour. Thereafter the extract is filtered-off to remove it from the precipitate. The filtered extract is added with dichloroethane three times by portions of 10, 5 and 5 liters for 30 minutes. As a result, two layers are formed and xanthone glycosides are present in the upper layer. The layers are separated and water-saturated butanol is added to the upper layer in several portions: 10 liters—for the first extraction, 15 liters—for the second one and all subsequent extractions. There are carried out 3 extractions altogether, each lasting for 15 minutes. The combined butanolic solutions are evaporated in vacuum to the bottoms with the volume of 1/20 of the initial volume thereof. A residue of mangiferin is formed during evaporation which is placed into a refrigerator for 12 hours. Mangiferin is filtered-off, dried, disintegrated and recrystallized from a mixture dioxane-water (1:0.5). 0.1 kg of mangiferin is thus obtained. The yield of mangiferin is equal to 1.0% by weight of the starting stock.

EXAMPLE 3

10 kg of threshed disintegrated grass of *Hedysarum alpinum L.* with a particle size of not more than 2 mm are treated at room temperature and under continuous stirring for 10 minutes with a mixture of acetone-water (1:0.5) at the ratio between the starting stock and the solvent of 1:15. There are obtained 120 liters of a water-acetone extract. The starting feedstock is repeatedly extracted under the same conditions with 120 liters of the same mixture. The second water-acetone extract is used for extraction of a fresh portion of the feedstock. The first water-acetone extract is evaporated in vacuum to give bottoms having volume of ¼ of the initial extract volume. The evaporated extract is filtered to remove the precipitated chlorophyll, resins and the like under stirring. The filtered-off extract is acidified with sulphuric acid to the pH of 4.0 and refluxed for 2 hours and then cooled to room temperature under stirring for 3 hours. Thereafter the filtration of the extract is effected to remove it from the precipitate. To the filtered-off extract dichloroethane is added three times in portions by 10, 5 and 5 liters for 30 minutes. As a result, two layers are formed, the upper one containing xanthone glycosides. The layers are separated and the upper layer is added with water-saturated butanol in several portions: 10 liters—for the first extraction, 15 liters—for the second and each of all subsequent extractions. There are carried out 7 extractions altogether, each lasting for 40 minutes. The combined butanolic solutions are evaporated in vacuum to give the bottoms having volume equal to 1/60 of the initial extract volume. A residue of mangiferin is formed during evaporation which is placed into a refrigerator for 24 hours. Mangiferin is filtered-off, dried, disintegrated and recrystallized from a mixture dioxane-water (1:2). There are obtained 0.1 kg of mangiferin. The yield of mangiferin is 1.0% by weight of the starting feedstock.

EXAMPLE 4

10 kg of threshed disintegrated grass of *Hedysarum flavescens Rgl. et Schmalh* with a particle size of not more than 3 mm are treated with a mixture of acetone-water (1:1) under continuous stirring at room temperature for 15 minutes at the ratio between the starting feedstock and the solvent of 1:17. There are obtained 140 liters of a water-acetone extract. The feedstock is again extracted under the same conditions using 140 liters of the same mixture. The second water-acetone extract is used for extraction of a fresh portion of the feedstock. The first water-acetone extract is evaporated in vacuum to give bottoms having volume equal to 1/5 of the initial extract volume. The evaporated extract is filtered to remove precipitated chlorophyll, resins and the like. The filtered-off extract is acidified with sulphuric acid to the pH of 2.9 and heated at reflux for one hour and then cooled to room temperature under stirring for 2 hours. Thereafter the formed precipitate is separated by filtration. The filtered-off extract is added with dichloroethane three times in portions by 10, 5 and 5 liters for 30 minutes. As a result, two layers are formed, the upper one containing xanthone glycosides. The layers are separated and to the upper one water-saturated butanol is added in several portions: 10 liters for the first extraction, 15 liters—for the second and each of all subsequent extractions. There are carried out 5 extractions altogether, each lasting for 30 minutes. The combined butanolic solutions are evaporated in vacuum to give the bottoms having volume equal to 1/40 of the initial extract volume. A residue of mangiferin is formed during evaporation which is placed into a refrigerator for 17 hours. Mangiferin is filtered-off, dried, disintegrated and recrystallized from a mixture dioxane-water (1:1) to give 0.1 kg of mangiferin. The yeld of mangiferin is equal to 1.0% by weight of the starting feedstock.

EXAMPLE 5

10 kg of threshed finely divided grass of *Hedysarum flavescens Rgl. et Schmalh* with a particle size of not more than 5 mm are extracted under continuous stirring at room temperature for 30 minutes with a mixture acetone-water (1:2) at the ratio between the starting feedstock and the solvent of 1:20. There are obtained 170 liters of a water-acetone extract. The feedstock is repeatedly extracted under the same conditions using 170 liters of the same mixture. The second water-acetone extract is used for extraction of a fresh portion of the starting feedstock. The first water-acetone extract is evaporated in vacuum to give the bottoms having volume equal to 1/6 of the initial extract volume. The evaporated extract is filtered to remove it from precipitated chlorophyll, resins and the like. The filtered-off extract is acidified with sulphuric acid to the pH of 2.0 and heated at reflux for 0.5 hour and then cooled to room temperature under stirring for one hour. Thereafter, the precipitate is separated from the extract by filtration. To the filtered extract dichloroethane is thrice added in portions by 10, 5 and 5 liters for 30 minutes. As a result, two layers are formed, the upper one containing xanthone glycosides. The layers are separated, to the upper one water-saturated butanol is added in several portions: 10 liters for the first extraction, 15 liters for the second and each of the subsequent stages. There are carried out 3 extractions altogether, each lasting for 15 minutes. The combined butanolic solutions are evaporated in vacuum to give the bottoms having volume equal to 1/20 of the initial value. During evaporation a residue of mangiferin is formed which is placed into a refrigerator for 12 hours. Mangiferin is filtered-off, dried, disintegrated and recrystallized from a mixture dioxane-water (1:0.5) to give 0.1 kg of mangiferin. The yield of mangiferin is 1.0% by weight of the starting feedstock.

EXAMPLE 6

10 kg of threshed disintegrated grass of *Hedysarum flavescens Rgl. et Schmalh* with a particle size of not more than 2 mm are treated with a mixture of acetone-water (1:0.5) under continuous stirring for 10 minutes at room temperature and at the ratio between the starting feedstock and the solvent of 1:15. There are obtained 120 liters of a water-acetone extract. The feedstock is repeatedly treated under the same extraction conditions using 120 liters of the same mixture. The second water-acetone extract is used for extraction of a fresh portion of the starting feedstock. The first water-acetone extract is evaporated in vacuum to give the bottoms having volume equal to ¼ of the initial extract volume. The evaporated extract is purified from the precipitated chlorophyll, resins and the like by filtration. The filtered-off extract is acidified with sulphuric acid to the pH of 4.0 and heated at reflux for 2.0 hours, followed by cooling to room temperature for 3 hours under stirring. Thereafter the extract is filtered-off to remove the formed precipitate. To the filtered extract dichloroethane is three times added in portions by 10, 5 and 5 liters for 30 minutes. As a result, two layers are formed, the upper one containing xanthone glycosides. The layers are separated and water-saturated butanol is added to the upper layer in several portions: 10 liters—for the first extraction, 15 liters—for the second and each of all subsequent extractions. There are carried out 7 extractions altogether, each lasting for 40 minutes. The combined butanolic solutions are evaporated in vacuum to give the bottoms having volume equal to 1/60 of the initial extract volume. During evaporation a residue of mangiferin is formed which is placed into a refrigerator for 24 hours. Mangiferin is filtered-off, dried, disintegrated and recrystallized from a mixture of dioxane and water (1:2) to give 0.1 kg of mangiferin.

The yield of mangiferin is 1.0% by weight of the starting feedstock.

What is claimed is:

1. In a process for the solvent extraction of mangiferin from a plant of the genus Hedysarum, the improvement which comprises comminuting the aerial portion of a plant selected from the species *Hedysarum alpinum L.* and *Hedysarum flavescens Rgl. et. Schmalh* to provide finely divided particles, having a particle size from 2 to 5 mm., treating the said plant particles, at a plant:solvent ratio of from 1:10 to 1:20, with an acetone-water mixture having an acetone:water ratio of 1:0.5 to 2 to extract xanthone glycosides therefrom, concentrating the resulting extract by evaporation to ¼ to 1/6 of its initial volume, filtering the concentrated extract to remove precipitated insolubles, acidifying the resulting filtrate with sulphuric acid to a pH value of from 2 to 4, heating the resulting filtered extract under reflux and, after cooling to room temperature, treating the resulting extract with a non-polar organic solvent selected from the group consisting of chloroform and dichloroethane to form two layers, the upper aqueous layer containing xanthone glycosides, treating the said upper aqueous layer with butanol, to form two layers therefrom, the upper layer of which comprises a solution of xanthone glycoside in butanol, evaporating the solvent from the said upper butanol layer, separating the resulting precipitated mangiferin and recrystallizing the said mangiferin.

* * * * *